United States Patent [19]

Charudattan

[11] 4,162,912

[45] Jul. 31, 1979

[54] COMPOSITION AND PROCESS FOR CONTROLLING MILKWEED VINE

[75] Inventor: Raghavan Charudattan, 8520 NW. 2nd Pl., Gainesville, Fla. 32601

[73] Assignee: Raghavan Charudattan, Gainesville, Fla.

[21] Appl. No.: 875,846

[22] Filed: Feb. 7, 1978

[51] Int. Cl.² .............................................. A01N 9/00
[52] U.S. Cl. ...................................................... 71/79
[58] Field of Search ............................................ 71/79

[56] References Cited

PUBLICATIONS

DeBach, Biological Control of Insect Pests and Weeds, p. 637 (1964).

*Primary Examiner*—Catherine L. Mills
*Attorney, Agent, or Firm*—Robert L. Niblack; Gildo E. Fato

[57] ABSTRACT

Disclosed is a composition and method for controlling milkweed vine by applying Araujio mosaic virus to the vine.

5 Claims, No Drawings

COMPOSITION AND PROCESS FOR CONTROLLING MILKWEED VINE

BACKGROUND OF THE INVENTION

As an alternative to chemical pest control, the use of naturally occurring biological agents provide many advantages. The use of biologicals should reduce the environmental impact of chemicals as well as providing safety advantages to non-target life forms. The use of native plant pathogens for biological control of weeds can be considered as a specific alternative to chemical herbicides. The native pathogen in the natural state exists along with its host and, of necessity, must not be totally destructive in the native habitat or the pathogen too would disappear. However, it should be possible to use a pathogen, which normally is native, in such a way as to overcome the host defenses and produce sufficient disease in the host to affect biological control.

This invention relates to the use of a naturally occurring virus (*Araujia mosaic* virus) and its formulation as a biological control agent of the noxious weed, milkweed vine (*Morrenia odorata*).

The milkweed vine is a serious weed pest in citrus and is not adequately controlled by chemical herbicides. The weed is rapidly spreading and presently infests approximately 300,000 acres in the central fruit-growing area of Florida.

DETAILED DESCRIPTION OF THE INVENTION

The *Araujia mosaic* virus (AMV) was detected as conspicuous mosaic symptoms in Argentina in 1975. The virus was infecting a plant, (*Araujia angustifolia*), which is closely related (family Asclepiadaceae) to *Morrenia odorata*. The virus was brought to the United States under quarantine auspices of the USDA and established on *Morrenia odorata* in a quarantine greenhouse at the University of Florida.

*Araujia mosaic* virus (AMV) is easily inoculated on to healthy milkweed vine (*Morrenia odorata*) by rubbing its leaves with virus containing sap or with buffer extracts of purified virus.

Manual inoculation is accomplished with one of two types of virus inoculums.

(i) Infected leaves.

About 2 g of AMV infected leaves are ground in 2 to 5 ml of 0.025 Molar borate buffer at pH 8.2 and 500 mg. of a fine abrasive powder like the Carborundum powder. Borate buffer consists of 50 ml of sodium borate, $Na_2B_4O_7 \cdot 10 H_2O$ at 9.525 g/liter of distilled water, 18.8 ml of 0.1 Molar HCl and 31.2 ml of distilled water. Healthy plants of *M. odorata* are inoculated by dusting newly expanded leaves with Carborundum powder and gently rubbing them with a cheesecloth strip soaked in virus containing sap. About 5 ml of this inoculum will be sufficient to inoculate about 50 plants. Four to six leaves per plant are rubbed in this manner.

(ii) Purified virus preparation.

AMV can be processed to yield a pure preparation of the virus. Purified AMV can be inoculated on its host by suspending the virus preparation at about 10 µg per ml of the borate buffer and rubbing the resulting inoculum on leaves as mentioned above.

Virus infected leaves or purified viruses can be stored for several years in a lyophilized state without loss in infectivity. AMV has been stored in this manner since 1975 without losing infectivity. However, fresh virus containing sap or the buffer extract of the virus can be stored only up to 72 hours at room temperature. Freshly prepared AMV extracts will withstand temperatures up to 50° C., but will be inactivated between 51° and 60° C. Hence, the best method of storage of AMV is lyophilization.

Inoculated *M. odorata* seedlings show virus symptoms in about 7 to 10 days after inoculation. First signs of symptoms are seen in newly expanding leaves. After about two weeks, generally all leaves above the point of inoculation show symptoms, indicating that the virus is well established on the host. The virus is recoverable after this stage from symptomatic leaves at all times.

In a greenhouse study, the persistence of AMV in *M. odorata* led to a decrease in the aerial, photosynthetic areas of the plant. In comparison with healthy, control plants, AMV-infected *M. odorata* plants registered the following percentages of reduction.

Leaf length 3.72; leaf width 9.26; plant height 12.77; fresh weight 18.78 and dry weight 27.78

These values, especially the 18.78% reduction in the fresh weight and the 12.77% in the height of the plant suggested that the virus led to a less "luxurious" growth of *M. odorata* which may significantly affect the plant's ability of compete in the field. The field observations on AMV infected plants in Argentina would clearly support this hypothesis.

The biological herbicide described herein may be utilized effectively in diverse formulations including the agronomically acceptable adjuvants and carriers normally employed for facilitating the dispersion of active ingredients for agricultural applications recognizing that the dosage, formulation, mode of application of such an agent and other variables may affect its activity in any given application. Thus, the described biological herbicide may be formulated as a suspension or dispersion, in aqueous or now-aqueous media, as a dust or wettable powder, as an emulsifiable concentrate, or as any of several other known types of formulations, depending on the desired mode of application. Preferably, the plant is manually or mechanically injured prior to application of the herbicide to thereby facilitate infection by the virus.

What is claimed is:

1. A biological herbicide composition for the control of milkweed vine said composition comprising: *Araujia mosaic* virus and an agronomically acceptable carrier.

2. The composition of claim 1 wherein the virus is in the form of an extract from an infected plant.

3. The composition of claim 1 wherein the carrier comprises a borate buffer.

4. A method for controlling the growth of milkweed vine said method comprising applying *Araujia mosaic* virus to the milkweed vine plant.

5. The method of claim 4 wherein said milkweed vine is injured prior to application of said virus.